United States Patent [19]

Sholder

[11] Patent Number: 5,010,893

[45] Date of Patent: * Apr. 30, 1991

[54] MOTION SENSOR FOR IMPLANTED MEDICAL DEVICE

[75] Inventor: Jason A. Sholder, Canoga Park, Calif.

[73] Assignee: Siemens-Pacesetter, Inc., Sylmar, Calif.

[*] Notice: The portion of the term of this patent subsequent to Sep. 20, 2005 has been disclaimed.

[21] Appl. No.: 172,610

[22] Filed: Mar. 24, 1988

Related U.S. Application Data

[63] Continuation-in-part of Ser. No. 3,433, Jan. 15, 1987, Pat. No. 4,771,780.

[51] Int. Cl.$^5$ .............................. A61N 1/36
[52] U.S. Cl. .............................. 128/782; 128/419 PG; 200/61.45 R; 200/61.52; 200/DIG. 2; 200/DIG. 30; 340/573; 340/686; 340/689
[58] Field of Search .................. 200/61.45 R, 61.52, 200/DIG. 29, 2, 30; 340/573-576, 686, 689; 128/419 PG, 782, 423 W

[56] References Cited

U.S. PATENT DOCUMENTS

| | | | |
|---|---|---|---|
| 3,083,712 | 4/1963 | Keegan, Jr. | 128/423 W |
| 3,161,856 | 12/1964 | Kirby . | |
| 3,204,637 | 9/1965 | Frank et al. | 128/423 |
| 3,520,200 | 7/1970 | Rodgers | 200/61.45 R |
| 3,539,740 | 11/1970 | Isenor et al. | 200/DIG. 24 |
| 3,557,796 | 1/1971 | Keller, Jr. et al. | 128/419 |
| 3,593,718 | 7/1971 | Krasner et al. | 128/419 P |
| 3,760,733 | 11/1973 | Marchsando | 200/61.45 R |
| 3,935,669 | 2/1976 | Potrzuski et al. | 200/61.45 R |
| 3,943,936 | 3/1976 | Rasor et al. | 128/419 P |
| 4,018,861 | 10/1976 | Gettens et al. | 128/903 |
| 4,112,926 | 9/1978 | Schulman et al. | 128/782 |
| 4,140,132 | 2/1979 | Dahl | 128/419 PG |
| 4,198,990 | 4/1980 | Higgins et al. | 128/782 |
| 4,202,339 | 5/1980 | Wirzfield et al. | 128/419 PG |
| 4,228,803 | 10/1980 | Rickiards | 128/419 PG |
| 4,284,986 | 8/1981 | Amortegui | 340/573 |
| 4,428,378 | 1/1984 | Anderson et al. | 128/419 PG |
| 4,436,092 | 3/1984 | Cook et al. | 128/419 PG |
| 4,567,892 | 2/1986 | Plicchi et al. | 128/419 PG |
| 4,596,251 | 6/1986 | Plicchi et al. | 128/419 PG |
| 4,722,342 | 2/1988 | Amundson . | |
| 4,782,836 | 11/1988 | Alt . | |

OTHER PUBLICATIONS

Matula et al., "A New Mechanical Sensor for the Detection of Body Activity and Posture Suitable for Rate Responsive Pacing", *PACE*, vol. 10 (Sep.-Oct. 1987).

*Primary Examiner*—Stephen C. Pellegrino
*Assistant Examiner*—David Shay
*Attorney, Agent, or Firm*—Bryant R. Gold; Malcolm J. Romano

[57] ABSTRACT

A motion sensor for use within an implantable medical device provides a digital output signal that can be connected directly to the digital processing and control circuits of a pacemaker or other device. This signal may be used to adjust the basic pacing rate of the pacemaker as a function of the physical motion or activity that is sensed. The motion sensor includes an enclosed housing having conductive element therein that partially fills the space of a cavity within the enclosed housing. The conductive element is free to roll, flow or otherwise move around the inside of the housing in response to external forces. The external forces that cause the conductive element to move include the physical motion of the patient as well as the force of gravity. As the conductive element moves within the enclosed housing, it makes electrical contact with at least two of three electrodes that are selectively spaced around the inside periphery of the housing. By monitoring whether and for how long an electrical contact is made or broken between electrodes, a determination is thus made relative to the movement of the conductive element within the housing, and the rapidity with which such movement occurs. This sensed motion is directly related to the physical activity or movement of the patient.

15 Claims, 1 Drawing Sheet

MOTION SENSOR FOR IMPLANTED MEDICAL DEVICE

BACKGROUND OF THE INVENTION

This application is a continuation-in-part of application Ser. No. 003,433, filed Jan. 15, 1987 now U.S. Pat. No. 4,771,780.

The present invention relates to implanted pacemakers, and more particularly to an implanted pacemaker that includes a motion or activity sensor for sensing the physical motion or activity of a patient in whom the pacemaker has been implanted.

Pacemakers are used to provide an electrical stimulus to the heart in the absence of normal heart activity in order to keep the heart beating at a safe level. In turn, a heart that beats at a safe level maintains an adequate supply of blood to the body tissue, thereby providing the needed supply of oxygen to the body cells and removing wastes from the body cells—in short, to keep the body cells alive, and hence to keep the patient alive.

As the physiological activity of the patient increases, many of the body cells must work harder, thereby requiring an increased supply of oxygen and an increased removal of carbon dioxide. In a normal healthy person, this increased supply of oxygen is provided by the heart and/or lungs increasing their respective rates of volumetric flow, i.e., by the heart increasing the rate and/or efficiency with which it pumps the blood through the body, and by the lungs increasing the rate and/or efficiency with which they inhale and exhale oxygen and carbon dioxide.

In some patients with a pacemaker, however, the heart may not be able to respond to a physiological need to pump more blood because of the heart's dependency on a stimulus from the pacemaker in order to beat (contract or depolarize). Accordingly, for these pacemaker patients, there is a need to make the pacemaker sensitive to physiological demands so that the pacemaker-provided stimulus can be provided in accordance with these demands. If this need can not be not met, as has often been the case with prior art pacemakers, then the patient must be cautious and limit his or her physical activity so that the physiological demands are kept within safe limits. Unfortunately, this limitation may severely restrict the physical activity of a pacemaker patient.

Recognizing this need, prior art pacemakers have been developed that are programmable, i.e., the basic rate at which the stimulation pulses are provided by the pacemaker can be noninvasively changed. Such programming, however, while extremely useful in many ways, has not been totally satisfactory because it still requires that a programming change be made, and such changes can typically only be made by a physician or other technician having the proper equipment. Moreover, even if the patient has access to the proper programming equipment, the patient can not always know when his or her physiological demands will be changing. Hence, there is a need in the art to provide a pacemaker that automatically responds to the physiological demands of the patient so that the needed pacemaker-provided stimuli can be provided at the appropriate times and at the appropriate rates.

Automatic physiologically-responsive pacemakers are known in the art. Such pacemakers have relied on numerous and varied sensed parameters as a physiological indicator that the demands of the patient are changing. For example, it is known in the art to measure blood temperature (see U.S. Pat. No. 4,436,092), blood oxygen concentration (see U.S. Pat. No. 4,202,339), repolarization interval (see U.S. Pat. No. 4,228,803), respiration rate (see U.S. Pat. Nos. 3,593,718 and 4,567,892), minute ventilation (see U.S. patent 4,596,251), physical activity as sensed by a piezoelectric element (see U.S. Pat. Nos. 4,140,132 and 4,428,378) and the depolarization interval (see U.S. Pat. No. 4,712,555) as parameters that indicate a change in physiological need.

For purposes of the present invention, it is the physical activity of the patient, as sensed by measuring the motion or movement of the patient, that comprises the physiological parameter to be used for controlling the rate of a pacemaker.

As indicated above, some attempts are known in the art for causing a pacemaker to sense and respond to physical activity. Using a piezoelectric element, as is taught in the U.S. Pat. No. 4,428,378 patent, for example, requires that the electrical analog signal from the piezoelectric element be processed in a prescribed manner. While such processing can be done, it requires special filtering and thresholding circuitry, all of which adds to the bulk and power consumption of the pacemaker. Needless to say, keeping power consumption and size to a minimum is a primary goal of all implantable pacemaker design. Hence, any added circuits which tend to increase the size, bulk, or power consumption of a pacemaker are disfavored.

Further, there are other disadvantages to using a piezoelectric element as a sensor of physical activity. For example, depending upon how the piezoelectric crystal is physically constructed and/or oriented within the patient, it may be less sensitive to physical movement in a given direction (X, Y or Z axis) than to movement in another direction. Further, whenever an analog signal is sensed, such as the signal from a piezoelectric element, it usually must eventually be converted to some sort of digital signal that can interface with the basic digital circuits used to realize modern pacemaker circuits. While analog-to-digital circuits are well known in the art, they too add to the bulk and power consumption of the pacemaker.

Where an acoustic pickup device is employed in conjunction with a mechanical device, which mechanical device is designed to generate various sounds as a function of physical activity, such as is disclosed in the U.S. patent application Ser. No. 07/192,609, an analog-to-digital conversion must still occur. Further, an added element (the mechanical device that serves as the source of the acoustic signal and/or the microphone pickup element) must be included within the pacemaker.

Accordingly, what is needed is a way of detecting physical activity or body motion using a simple detector device that can interface directly with the digital circuits of the pacemaker and that does not noticeably add to the complexity, bulk, or power consumption of the pacemaker.

Finally, it is noted that even though a dual chamber pacemaker (i.e., one that can provide stimulation pulses to both chambers of the heart) may theoretically be operable in a mode that is responsive to the physiological demands of some patients, there may be practical reasons why such a dual chamber pacemaker is not used. For example, in a patient with complete heart block, a dual chamber pacer operating in the DDD mode of operation (i.e., the pacemaker paces in both the atrium and ventricle, and senses in both the atrium and ventricle) will respond to the heart's natural pacemaker—the SA (Sinoatrial) Node. This occurs because the atrium responds to the SA Node and causes the atrium to contract. The atrial sensing circuits of the DDD pacemaker sense this contraction and, after an appropriate AV delay, generate a ventricular stimulation pulse that causes the ventricle to contract. Thus, the DDD pacer guarantees rate responsiveness and AV synchrony. However, as indicated, there may be some circumstances where a DDD pacemaker would not be used. Hence, for these patients, there is still a need for a single chamber pacemaker that is automatically responsive to the patient's physiological needs.

In the description of the invention that follows, it is noted that in general no distinction will be made between whether a single chamber or a dual chamber pacemaker is used. This is because the motion or activity sensor described herein can be used with either type of pacemaker.

SUMMARY OF THE INVENTION

The present invention is directed to an implantable pacemaker (or other implanted medical device) that includes a body motion sensor as a part thereof. Using the output from the motion sensor as an indicator of the patient's physiological need, the rate at which the pacemaker provides stimulation pulses to the heart can be appropriately adjusted.

The motion sensor of the present invention provides a digital signal as an output signal. The frequency or period of this digital signal represents the motion activity of a patient to whom the sensor is attached. Thus, this signal can be connected directly into the digital processing circuits of the medical device with which it is used without the need for using additional analog-to-digital conversion circuits.

The motion sensor comprises a sealed housing having a cavity therein into which an electrically conductive element is placed. This electrically conductive element does not fill the cavity and is allowed to freely roll or move therein when subjected to external forces, such as the force of gravity, or any movement of the patient. Protruding into the cavity is a plurality of electrodes, each of which respectively makes momentary electrical contact with the moving conductive element and each of which is electrically accessible from a point exterior to the housing. The size of the conductive element and the construction of the cavity in which it is placed are such that the conductive element makes momentary electrical contact with at least two electrodes simultaneously. Thus, by making appropriate electrical connections to the electrodes from the outside of the housing, a determination can be made as to the position of the conductive element within the housing relative to the position of the electrodes. More significantly, by monitoring the electrodes external to the housing, a determination can be made as to any movement of the conductive element within the housing and the rapidity with which the movement occurs. Which movement is directly related to the physical motion or activity to which the sensor is subjected.

By placing a sensor as above described within or on the patient, the detected movement of the conductive element can thus be used as an indication of the physical motion of the patient. This is because the external forces that act upon the conductive element to cause it to move include the physical motion of the patient. That is, in operation, the conductive element always moves to a position closest to the earth's gravitational pull by the gravity force vector. The conductive element is forced away from this position by any motion of the patient not in perfect alignment with the gravity force vector patient, whether walking, talking, running, or merely breathing, will only be in alignment with the gravity vector, if at all, for extremely short periods of time, it is possible by monitoring the motion of the conductive element over time to obtain an accurate indication of the patient's motion. Further, by suitably processing the signals generated by such a sensor, it is generally possible to distinguish, and therefore separate, those signals caused by external forces that do not include the physical motion of the patient.

Advantageously, the physical movement of the patient in any direction (x, y or z axis) can be detected by the physical motion sensor of the present invention (providing none of these axes are in perfect alignment with the gravitational vector). Further, through appropriate electrical connections, the sensor generates a pulse-type signal (pulse train) in response to the sensed physical movement that is directly compatible with the pacemaker's digital circuits. Hence, no analog-to-digital conversion, or other analog filtering is required before the signal can be digitally processed. The frequency of occurrence, or more precisely the time period between successive pulse of the pulse train signal, provides an indication of the magnitude of the sensed physical motion.

From the above summary, it is thus seen that a primary feature of the present invention is to provide an implantable pacemaker that includes a physical motion sensor. The rate at which the pacemaker provides stimulation pulses to the heart, or the length of an escape interval (in the case of a demand-type pacemaker), is then varied in response to physical motion sensed by the motion sensor. Thus, through use of the motion sensor the pacemaker is made physiologically responsive to physical motion.

Another important feature of the present invention provides a motion sensor for use with a medical device that reliably signals the physical movement or activity of a patient to whom the motion sensor is attached. In a preferred embodiment, the indication provided by the sensor is an pulse signal that is compatible for use with digital circuits without the need for analog-to-digital conversion, buffer, or threshold circuits. Further, the sensor consumes little, if any, additional power beyond that of the pacemaker circuits. The sensor is advantageously small in size and can be readily included within the housing of a typical pacemaker or other implantable medical device.

BRIEF DESCRIPTION OF THE DRAWINGS

The above and other advantages and features of the present invention will be more apparent from the following more particular description thereof, presented in conjunction with the following drawings, wherein.

DETAILED DESCRIPTION OF THE INVENTION

The following description is of the best presently contemplated mode of practicing the invention. This description is not to be taken in a limiting sense but is made merely for the purpose of describing the general principles of the invention. The scope of the invention should be ascertained with reference to the appended claims.

Figure 1:
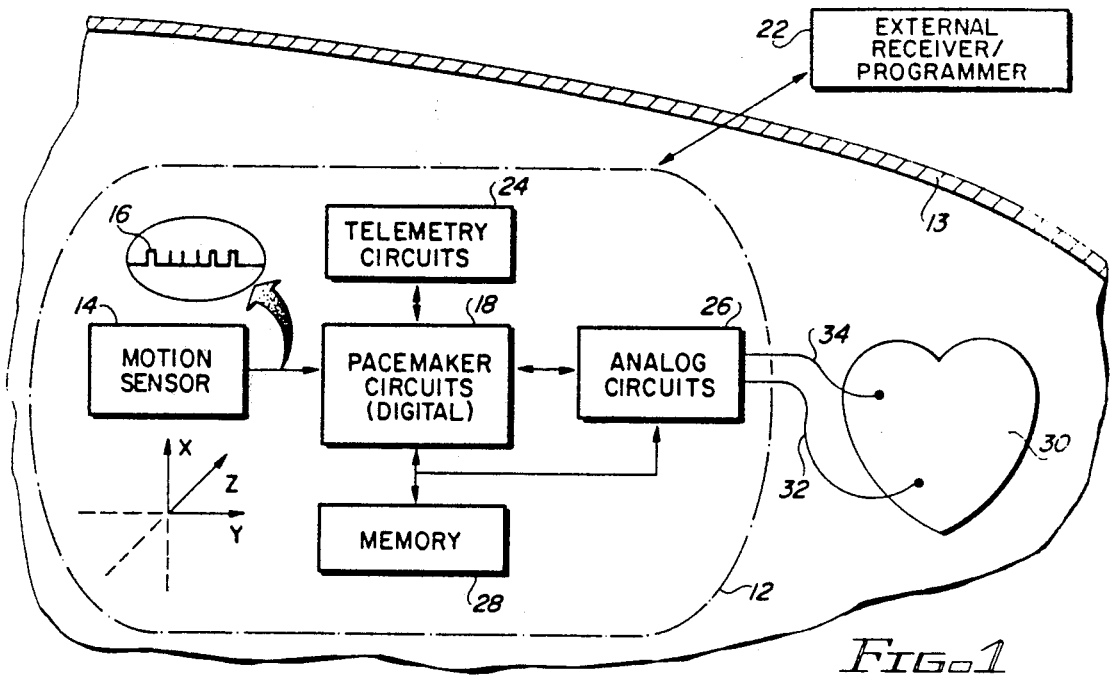
FIG. 1 is a block diagram of a pacemaker having a physical motion sensor in accordance with the present invention.

Referring first to FIG. 1, there is shown a block diagram of an pacemaker 12 that is implanted beneath the skin 13 of a patient. The pacemaker 12 includes a motion sensor 14. Any motion sensed by the sensor 14 is manifest by a digital signal 16 that is fed directly into the digital circuits 18 of the pacemaker. The digital circuits 18 determine when a stimulation pulse should be generated. Operating parameters that control when such a stimulation pulse is to be generated, in addition to the motion signal 16 (described more fully below), include control signals received from an external programmer through telemetry circuits 24, and cardiac activity sensed by analog circuits 26. Many of the control signals received through telemetry circuits 24 are stored in memory 28, as are other controlling parameters. In addition to being able to receive program control signals from the external programmer, the pacemaker 12 can also send signals through the telemetry circuits 24 that are received by an external receiver. As shown in FIG. 1, the external programmer and eternal receiver are typically combined into a single receiver/programmer device 22.

When the pacemaker circuits 18 have determined that a stimulation pulse is to be generated, a trigger signal is presented to the analog circuits 26. The analog circuits 26 respond to this trigger signal by generating a stimulation pulse of predetermined amplitude that is delivered to the heart 30 via lead 32 or 34. (It is noted that while two leads, 32 and 34, are shown in FIG. 1, for many applications only one lead would be required.) Conventional sensing circuits are also included within the analog circuits 26, thereby allowing the sensing of electrical activity occurring on leads 32 or 34 (e.g., an R-wave or P-wave).

With the exceptions as indicated below, the pacemaker 12 in FIG. 1 operates in conventional manner. Hence, in the description that follows, no additional detail will be provided relative to its operation, except with respect to how the digital pacemaker circuits 18 respond to the motion signal 16 generated by the sensor 14. Before explaining this response, however, it will be helpful to describe the sensor 14 and the manner in which the digital motion signal 16 is generated.

Figure 2:
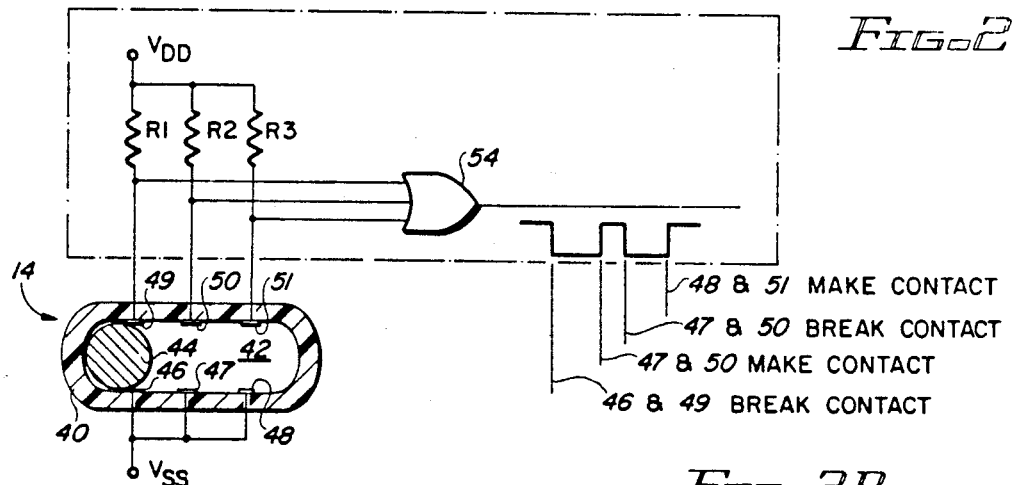
FIG. 2 is a simplified diagram of the motion sensor of the present invention.

Referring to FIG. 2, a simplified one-dimensional version of the sensor 14 is presented in order to explain the basic operating principles thereof. The sensor includes an enclosed housing 40 having a cavity 42 therein. This housing is made from a nonconductive material, such as glass. Inside the housing 40, within the cavity 42, a conductive element 44 is placed. This conductive element is allowed to freely move within the housing 44 as it is subjected to external forces, such as the force of gravity or forces caused by motion of the sensor 40. In the preferred embodiment, the cavity 42 is evacuated of all gases, i.e., it is a vacuum, and the conductive element 44 is a bead of liquid mercury. Any conductive material, whether a solid, liquid, or gas, could of course be used for this purpose so long as it moves within the cavity 42 when subjected to external forces. As the housing is tilted or otherwise moved due to the motion of the patient. The force of gravity (sometimes referred to herein as the gravity vector) causes the conductive element 44 to roll, flow, or slide to its lowest possible point within the cavity 42. As the patient moves in any direction not in perfect alignment with the force of gravity, forces are generated according to well-established laws of physics that force the conductive element 44 away from this lowest point.

Protruding into the cavity 42 are a plurality of electrodes. Six such electrodes 46-51 are shown in the drawing. The conductive element is sized, and the electrodes are spaced apart, such that the conductive element always makes momentary simultaneous contact with at least two of the electrodes.

To illustrate, in the simplified drawing of FIG. 2, the conductive element 44 is shown in electrical contact with electrodes 46 and 49. If the housing 40 were tipped so that the right side thereof became lower than the left side, thereby causing the force of gravity to move the conductive element 44 from the left to the right of the housing, or if some other force were applied so as to cause the conductive element to move left-to-right, the conductive element 44 would in sequence break the contact between electrodes 46 and 49, make and break contact with electrodes 47 and 50, and then make contact with electrodes 48 and 51. If electrodes 46-48 are externally connected to a common voltage potential Vss, and if electrodes 49-51 are each externally connected to a voltage potential Vdd through respective pull-up resistors R1-R3, and if each electrode 49-51 is also connected as an input to an OR gate 54, the output signal of OR gate 54 represents the motion of the conductive element 44 from the left side of the housing 40 to the right side. That is, as shown in FIG. 1, the signal will first be high (at the Vdd level) representing the making of contact between electrodes 46 and 49. It will then go low, representing the breaking of the contact between electrodes 46 and 49. It then goes high again, representing the making of contact between electrodes 47 and 50; and then goes low again, representing the breaking of contact between electrodes 47 and 50. Finally, it goes high, representing the making of contact between electrodes 48 and 51.

When the housing 40 is alternately titled or otherwise moved such that the left side is alternately higher and then lower than the right side, the gravity vector causes the conductive element 44 to move first left-to-right and then right-to-left within the cavity 42. Other forces could be applied to cause this same back-and-forth motion. In either event, such back-and-forth motion of the conductive element 44 causes the signal appearing at electrodes 49-51 (which signal can be considered as the output signal 16 of the sensor 14, see FIG. 1), to alternate between Vdd and ground as contact is made and broken between the various pairs of electrodes. This action, in turn causes a train of pulses to be generated at the output of gate 54. The width of the pulses and the interpulse spacing (time interval between adjacent pulses) are representative of the velocity of the conductive element 44 as it so moves.

It is noted that the OR gate 54 and pull-up resistors R1-R3 shown in the simplified diagram of FIG. 2, may comprise part of the digital logic circuits 18 of the pacemaker 12. As is known to those skilled in the art, the pull-up resistors R1-R3 may be very large in value, thereby keeping current flow to a minimum. Moreover, where CMOS circuits are used for the digital logic elements of the digital circuits, the equivalent of the pull-up resistors R1-R3 may be realized using other CMOS components, thereby effectively reducing any power consumption associated with the sensor 14 to extremely low values.

Figure 3A:
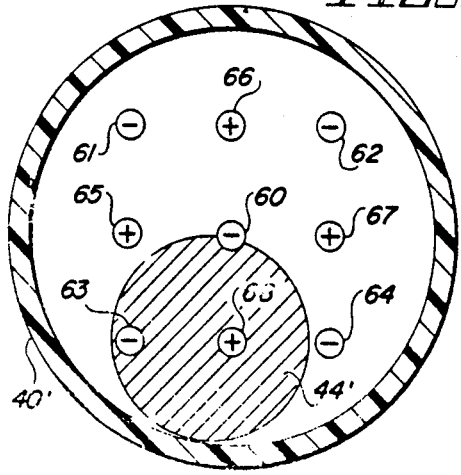
FIG. 3A is a cross-sectional view of a preferred embodiment of the motion sensor of the present invention.
Figure 3B:
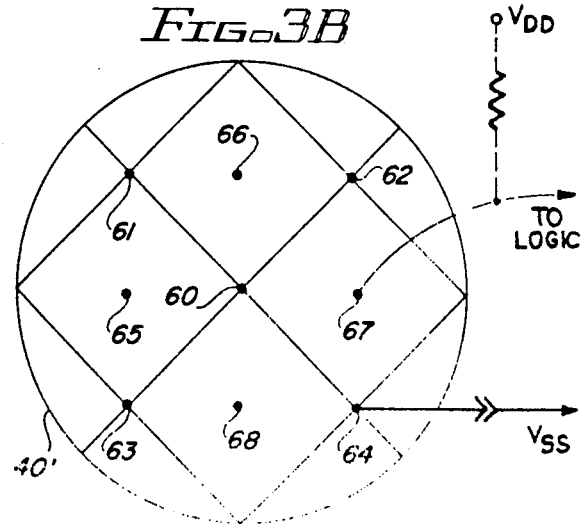
FIG. 3B is an outside view of the motion sensor of FIG. 3A.

Referring next to FIGS. 3A and 3B, a preferred construction of the sensor 14 is illustrated. In FIG. 3A, which is a cross-sectional view of the sensor, the housing 40' is a hollow sphere made from glass or other suitable nonconductive material. Selectively spaced around the periphery of the sphere housing 40' is a matrix of spaced-apart electrodes 60-68, only a portion of which are shown in the figure. Inside of the sphere a conductive element 44' is allowed to roll or flow. The preferred material for the conductive element 44' is mercury. As is known in the art, for all temperatures of concern, mercury is a liquid. When the inside of the spherical housing 40' is evacuated of all gases (i.e., made a vacuum), the liquid mercury behaves similar to a solid, and forms a bead that rolls or flows around the inside of the sphere 40', making and breaking electrical contact with two or more electrodes 60-68 as it rolls or flows. In FIG. 3A, the mercury bead 44' is shown in contact with electrodes 60, 63 and 68. Any motion of the patient will cause the mercury bead 44 to roll or flow so as to break electrical contact with these electrodes and make electrical contact with other electrodes.

The rolling or movement of the conductive element 44 can be detected by connecting the electrodes in a scheme such as that shown in FIG. 3B where the electrodes 60-64 are connected to a common reference potential Vss, and the electrodes 65-68 are connected to a different reference potential Vdd through respective pull-up resistors, or equivalent. (Thus, in FIG. 3A, the electrodes 60-64 are labeled "−", indicating they are tied to Vss, the most negative potential; and electrodes 65-68 are labeled "+", indicating they are coupled to Vdd, the most positive potential.) The "+" electrodes 65-68 are then also connected to the appropriate logic circuits. Whenever the voltage potential at a given electrode 65-58 is pulled to the Vdd potential, that indicates a connection has been broken between that electrode and an adjacent "−" electrode. Similarly, whenever the voltage potential at a given electrode 65-68 is pulled to the Vss potential, that indicates a connection has been made between that electrode and an adjacent "−" electrode by the conductive element 44' within the spherical housing 40'. Thus, by monitoring the "+" electrodes at the logic circuitry, as described in connection with FIG. 2, a signal is generated indicating the motion of the conductive element. Advantageously, this signal can be applied directly to the logic circuits without the need for any analog-to-digital conversion, threshold detection, or other analog processing.

As mentioned previously, the pulse width and interpulse interval (i.e., the period) of the pulse train generated by the sensor 14 of the present invention provide a measure of the physical motion of the patient. This is because the force of gravity causes the conductive element 44' to be pulled to its lowest possible position within the housing 40'. If the patient were able to hold perfectly still, without any motion whatsoever, the conductive element 44' would not move away from this rest position. (The term "rest position" is used herein to indicate that position to which the conductive element is forced by the gravity vector.) However, any physical activity or motion of the patient, no matter how slight, causes other forces to be generated that displace the conductive element 44' away from its rest position. The more vigorous the motion of the patient, the larger these forces become, thus causing the conductive element 44' to roll or move more rapidly within the housing 40'. This more rapid movement is reflected in a motion signal 16 having narrower pulse widths and a shorter interval between pulses.

The digital circuitry 18 processes the motion signal 16, using conventional techniques, in order to determine whether the signal has a high frequency (period) or short pulse width, or both. If so, a determination is made that the patient has begun a high activity phase. However, before altering the operation of the pacemaker, the digital circuits monitor the sensed activity to determine if this high activity phase continues over a prescribed period of time. For example, a short burst of a high frequency motion signal could be caused by something or someone simply bumping into the patient, and there would generally be no need to adjust the pacemaker's operation. However, if the high frequency motion signal continues for a prescribed period of time, such as 30-45 seconds, then the patient is probably moving more vigorously than normal, and an adjustment of the pacemaker's pacing rate (which includes adjusting the escape interval of a demand-type pacemaker) is in order.

The sensor 14 of the present invention, as indicated, responds to all motion of the patient, even talking and breathing. However, these lower-level motion activities can be distinguished because they will have an average frequency and/or pulse width associated therewith that can be detected. In operation, the digital processing circuits 18 will recognize this lower-level type of activity or motion and simply save it as a reference level. This reference level could, of course, change over a period of time. This reference level (and by "reference level" it is meant the frequency or period and/or average pulse width of the motion signal) could then be compared against the present motion signal level in order to determine if any significant changes exist that have been maintained for the requisite time period. If so, appropriate adjustments could be made, upward or downward as required, in the basic pacing rate set by the pacemaker.

While the invention described herein has been described with reference to a particular embodiment and application thereof, numerous variations and modifications could be made thereto by those skilled in the art without departing from the spirit and scope of the invention as claimed. Accordingly, the true scope of the invention should be determined with reference to the claims set forth below.

What is claimed is:

1. A body implantable motion sensor for use with a pacemaker, said sensor comprising:
   housing means for implantation in a body, said housing means comprising a housing containing electronic circuits, said housing including an enclosed non-conductive cavity therewithin having a plurality of conductive electrodes exposed on an inside wall of said enclosed non-conductive cavity;
   means responsive to the application of external forces for making and breaking electrical contact between at least two of said plurality of electrodes; and means for electrically monitoring said electrodes with said electronic circuits for determining when electrical contact is made therebetween.

2. The body implantable motion sensor of claim 1 wherein said making and breaking electrical contact means comprises a movable conductive element enclosed within said non-conductive cavity, said conductive element making respective electrical contact with said electrodes as said conductive element is moved within said cavity by the application of external forces to said housing, said plurality of electrodes being spaced apart from each other and positioned around the periphery of said cavity such that at least two of said electrodes will simultaneously be in contact with said conductive element as said conductive element moves within said non-conductive cavity.

3. The motion sensor of claim 2 wherein said cavity comprises a generally spherically-shaped cavity in which said conductive element may freely move in response to external forces in any direction.

4. The motion sensor of claim 2 wherein said conductive element comprises a conductive fluid.

5. The motion sensor of claim 4 wherein said conductive fluid comprises mercury.

6. An implantable digital motion sensor for use with a pacemaker, said pacemaker electrically coupled to said sensor for receiving a digital signal therefrom, said sensor generating a digital signal as a function of the physical motion to which said motion sensor is subjected, said digital signal being used by said pacemaker to indicate the amount of physical motion to which said pacemaker is subjected, said sensor comprising:

housing means for implantation in a body, said housing means comprising a housing affixed to said pacemaker, said housing having a plurality of electrodes therein;

means for making and breaking electrical contact with said plurality of electrodes as a function of external forces applied to said pacemaker; and means for coupling a voltage potential between said plurality of electrodes, said voltage potential having first and second voltage levels associated therewith, the voltage present at a given electrode thereby varying between said first and second voltage levels as a function of whether electrical contact has been made or broken between said given electrode and at least one other of said plurality of electrodes, said voltage at said given electrode comprising said digital signal.

7. The digital motion sensor of claim 6 wherein said digital signal comprises a pulse train, and further wherein the pulse width and time interval between adjacent pulses of said pulse train signal vary as a function of the physical motion to which said motion sensor is subjected.

8. The digital motion sensor of claim 7 wherein the pulse width of said pulse train gets narrower as a function of increased physical motion of said sensor.

9. The digital motion sensor of claim 7 wherein the time interval between adjacent pulses of said pulse train gets shorter as a function of increased physical motion of said sensor.

10. The digital motion sensor of claim 6 wherein said means for making and breaking electrical contact with said plurality of electrodes comprises a movable conductive element within said housing, said plurality of electrodes being spaced apart and positioned within said housing such that the conductive element makes momentary simultaneous electrical contact with at least two of said plurality of electrodes as the conductive element freely moves within said housing, the movement of said conductive element within said housing being caused by external forces applied to said motion sensor, said external forces including the force of gravity and forces caused by the movement of said sensor.

11. The digital motion sensor of claim 10 wherein said housing comprises an enclosed housing having a chamber therein into which said movable conductive element is placed, said housing being made from a nonconductive material.

12. The digital motion sensor of claim 11 wherein the chamber within said enclosed housing comprises a generally spherically-shaped chamber in which said conductive element may move in all directions.

13. The digital motion sensor of claim 11 wherein said movable conductive element comprises a conductive liquid.

14. A method of sensing the physical motion of a patient having a pacemaker comprising the steps of:

(a) placing a conductive element in a sealed housing, said housing having a plurality of electrodes spaced therein, said conductive element having a size that allows it to freely move within said housing when subjected to external forces, and to make simultaneous and momentary electrical contact with at least two of said electrodes as it moves within said housing;

(b) implanting said housing, conductive element, and electrodes within said patient;

(c) monitoring selected pairs of said electrodes to determine when electrical contact is made therebetween;

(d) measuring the time interval or frequency between the making of electrical contact between the electrodes of step (c); and (e) determining the change of the measurement of step (d), which change is indicative of the change in physical motion of the patient.

15. The method of sensing physical motion of claim 14 wherein step (d) further includes measuring the duration during which electrical contact is maintained between the electrodes of step (c).

* * * * *